United States Patent
Bridges

(10) Patent No.: US 7,111,580 B1
(45) Date of Patent: Sep. 26, 2006

(54) DEVICE FOR DETECTING THE PRESENCE OF A CHEMICAL CONTAMINANT

(75) Inventor: Robert Bridges, Crowthorne (GB)

(73) Assignee: MassTech International Limited, Crowthorne (GB)

(*) Notice: Subject to any disclaimer, the term of this patent is extended or adjusted under 35 U.S.C. 154(b) by 0 days.

(21) Appl. No.: 09/936,795

(22) PCT Filed: Mar. 15, 2000

(86) PCT No.: PCT/GB00/00959

§ 371 (c)(1),
(2), (4) Date: Feb. 19, 2002

(87) PCT Pub. No.: WO00/55598

PCT Pub. Date: Sep. 21, 2000

(51) Int. Cl.
*G01D 21/00* (2006.01)

(52) U.S. Cl. ..................................................... 116/206
(58) Field of Classification Search ............... 116/206, 116/200, DIG. 41, 201; 73/1.17, 40.5, 40; 436/3, 161
See application file for complete search history.

(56) References Cited

U.S. PATENT DOCUMENTS

| | | | | |
|---|---|---|---|---|
| 3,115,862 A | * | 12/1963 | Underwood, Jr. ............ 116/266 |
| 3,233,459 A | * | 2/1966 | Gleason et al. ............. 116/206 |
| 3,621,810 A | * | 11/1971 | Zuck, Jr. .................... 116/283 |
| 3,846,795 A | | 11/1974 | Jones ......................... 340/421 |
| 4,071,319 A | * | 1/1978 | Nugent ....................... 116/206 |
| 4,228,428 A | * | 10/1980 | Niedermeyer ............... 340/628 |
| 4,237,972 A | | 12/1980 | Lanmon, II ................. 166/54.5 |
| 4,271,120 A | | 6/1981 | Michaud ..................... 422/53 |
| 4,306,127 A | * | 12/1981 | Payne ........................ 200/61.04 |
| 4,335,615 A | | 6/1982 | Kalfa et al. ................. 73/799 |
| 4,628,252 A | | 12/1986 | Terhune et al. .............. 324/65 |
| 4,682,156 A | * | 7/1987 | Wainwright ................. 340/603 |
| 4,709,577 A | * | 12/1987 | Thompson ................... 436/3 |
| 4,710,353 A | * | 12/1987 | Tanaka et al. ................ 436/3 |
| 4,748,930 A | * | 6/1988 | Leichnitz ..................... 116/206 |
| 4,770,028 A | * | 9/1988 | Flippo, Jr. ................... 73/40.7 |
| 4,774,830 A | * | 10/1988 | Hulsman ..................... 73/49.3 |
| 4,893,498 A | * | 1/1990 | Jensen ......................... 73/49.2 |
| 5,030,033 A | * | 7/1991 | Heintzelman et al. . 405/129.57 |
| 5,072,621 A | * | 12/1991 | Hasselmann ............... 73/40.5 R |
| 5,146,778 A | * | 9/1992 | Hsu ............................ 73/61.41 |
| 5,174,150 A | * | 12/1992 | Mann ........................... 73/49.2 |
| 5,200,615 A | * | 4/1993 | Hopenfeld .................. 250/302 |

(Continued)

FOREIGN PATENT DOCUMENTS

FR 2.704.318 4/1993

(Continued)

OTHER PUBLICATIONS

European Patent Application No. 0 370 685, Beard et al., Pub. date May 30, 1990.*

*Primary Examiner*—Christopher W. Fulton
*Assistant Examiner*—Amy R. Cohen
(74) *Attorney, Agent, or Firm*—Patterson & Sheridan, L.L.P.

(57) ABSTRACT

The disclosure relates to a device for detecting the presence of a chemical contaminant. The device comprising a resilient indicator element which is biased into a first position and is anchored in the first position by means of a failure element. The failure element is made of a material which fails in the presence of a chemical to be detected, thereby releasing the indicator element from its first position and allowing it to move under its own resilience into a second position in order to provide an indication of the presence of the contaminant.

9 Claims, 4 Drawing Sheets

U.S. PATENT DOCUMENTS

| | | | | |
|---|---|---|---|---|
| 5,201,212 A | * | 4/1993 | Williams | 73/40.5 |
| 5,253,674 A | * | 10/1993 | Argyle et al. | 137/559 |
| 5,264,368 A | * | 11/1993 | Clarke et al. | 436/3 |
| 5,375,592 A | * | 12/1994 | Kirk et al. | 116/206 |
| 5,728,943 A | | 3/1998 | Colter, Jr. et al. | 73/799 |
| 5,792,661 A | * | 8/1998 | Cytron | 436/3 |
| 5,955,025 A | * | 9/1999 | Barrett | 116/206 |
| 6,479,294 B1 | * | 11/2002 | Fong et al. | 436/3 |

FOREIGN PATENT DOCUMENTS

| | | |
|---|---|---|
| JP | 57-067843 | 4/1982 |
| WO | 88/01052 | 2/1988 |

* cited by examiner

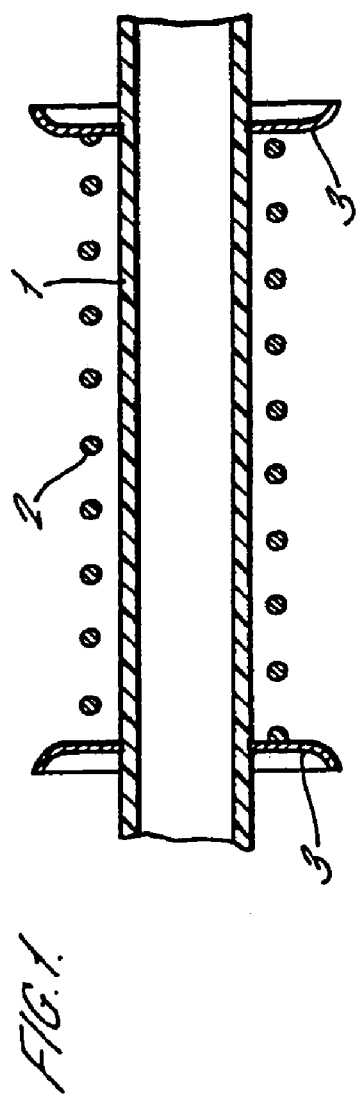
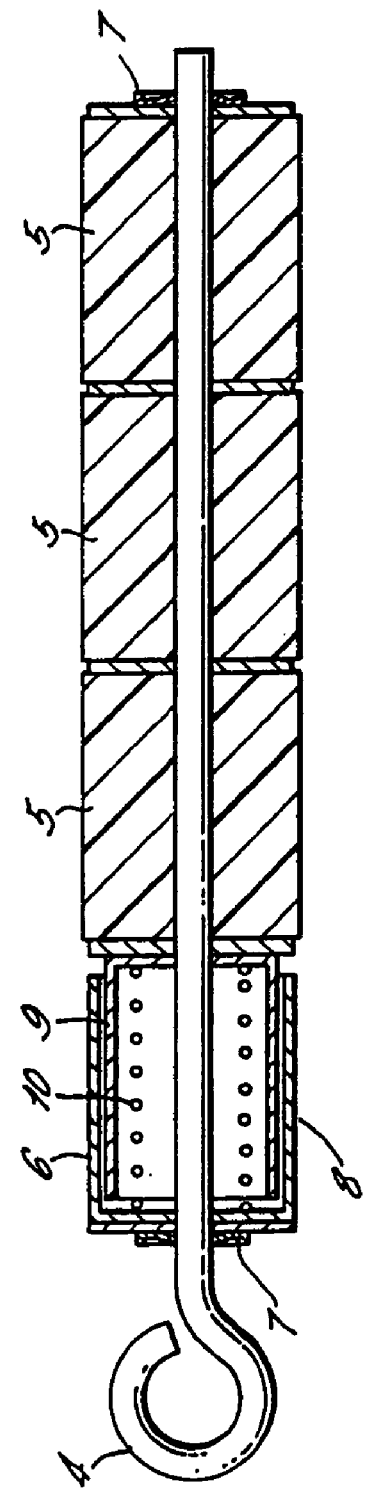

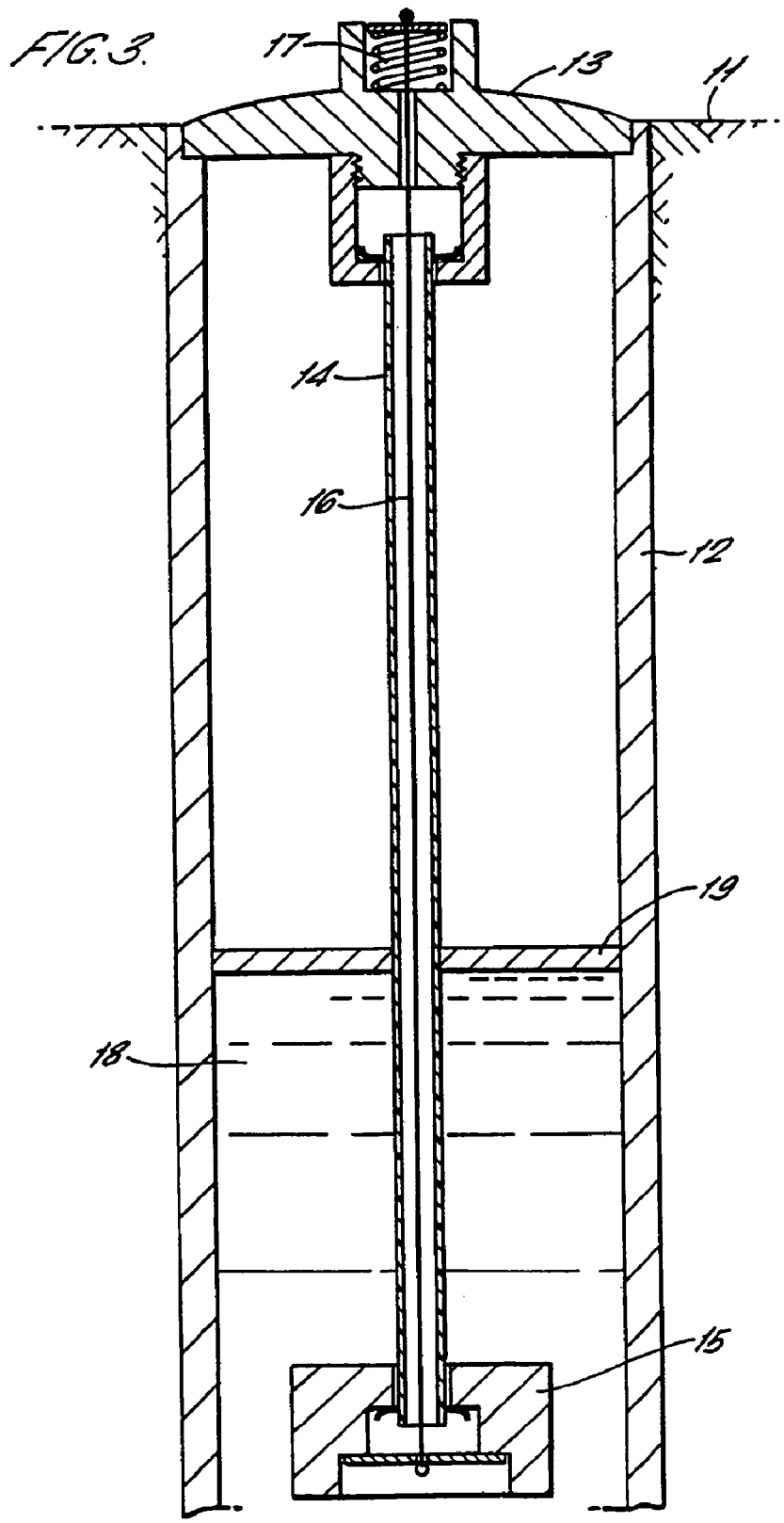

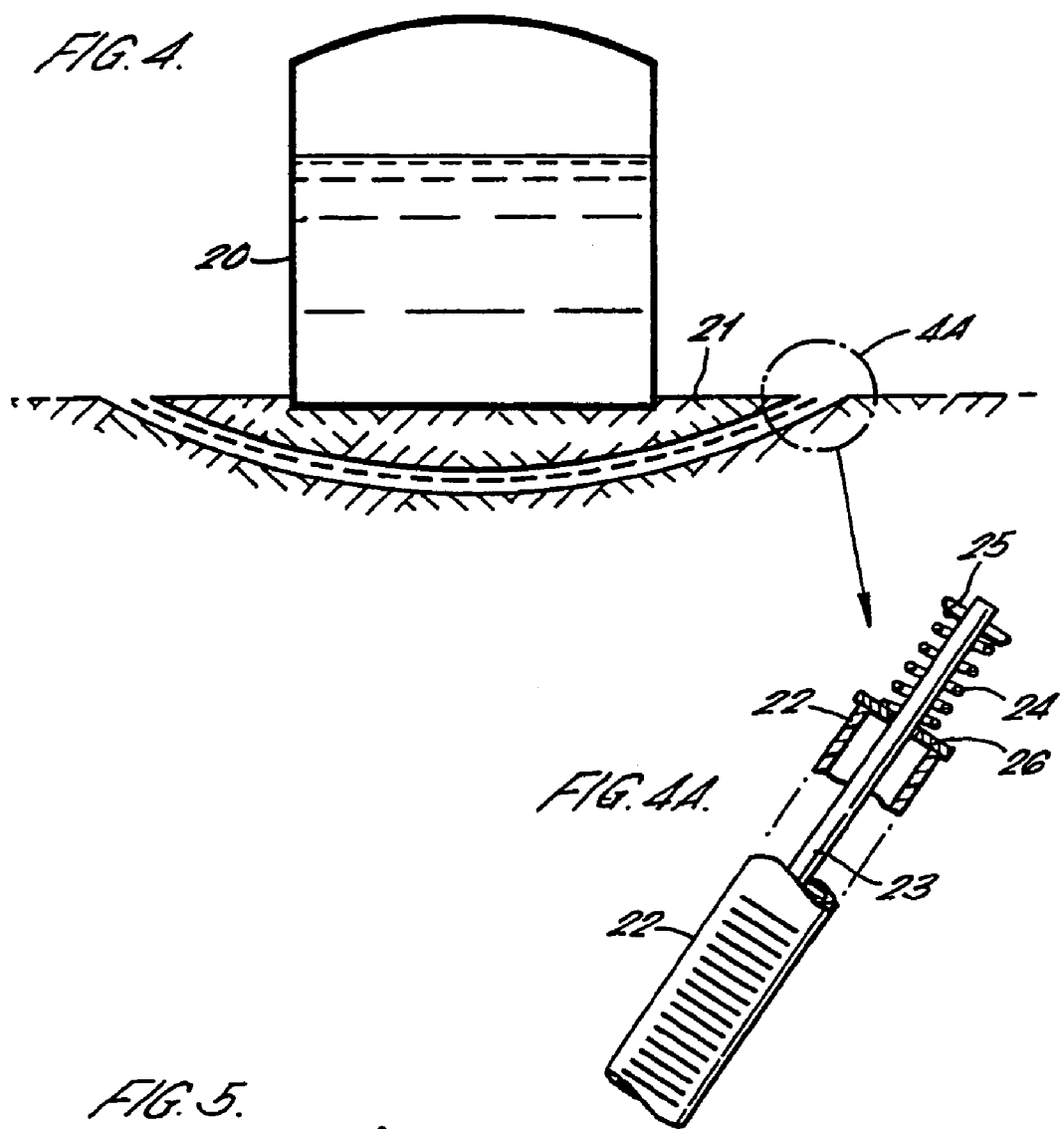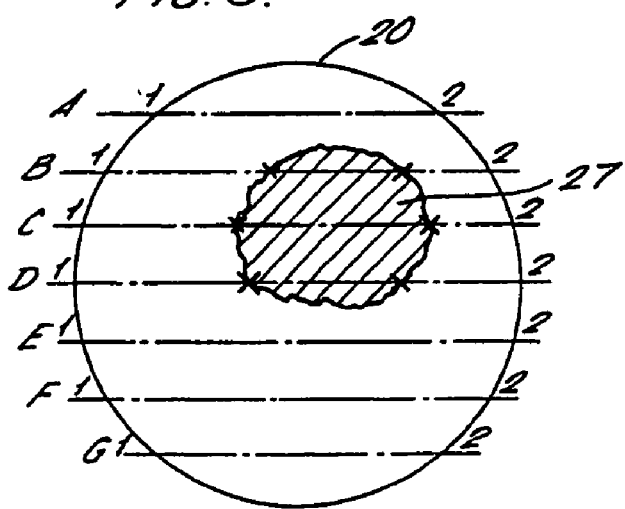

DEVICE FOR DETECTING THE PRESENCE OF A CHEMICAL CONTAMINANT

CROSS-REFERENCE TO RELATED APPLICATIONS

This application claims benefit of International Application No. PCT/GB00/00959, filed Mar. 15, 2000, and published under PCT Article 21(2) in English, and claims priority of Great Britain Application No. 9906014.7, filed on Mar. 16, 1999. The aforementioned applications are herein incorporated by reference in their entirety.

BACKGROUND OF THE INVENTION

1. Field of the Invention

The present invention relates to a device such as an indicator, switch or actuator for detecting the presence of a chemical contaminant. Such a detector is used, for example, in filling stations and chemical plants to detect the presence of unwanted chemicals.

2. Description of the Related Art

Chemical detection devices are frequently electronic and therefore have to be designed to be intrinsically safe making them prohibitively expensive for many applications and are dependent on the reliability of the power supply. Further, recent surveys in filling stations have shown that many of these devices have been physically disabled or no longer function for other reasons.

SUMMARY OF THE INVENTION

The present invention aims to provide a low cost, disposable device which does not require electricity.

According to a first aspect of the present invention there is provided a device for detecting the presence of a chemical contaminant, the device comprising an indicator element which is held in a first position by means of a failure element which is held in tension, the failure element being made of a material which fails in the presence of the chemical to be detected, thereby releasing the indicator element from its first position and allowing it to move into a second position in order to provide an indication of the presence of the contaminant.

According to a second aspect of the present invention, which may be independent of, or used in conjunction with the first aspect of the invention, there is provided a device for detecting the presence of a chemical contaminant, the device comprising a resilient indicator element which is held in a first position and is anchored in the first position by means of a failure element, the failure element being made of a material which fails in the presence of the chemical to be detected, thereby releasing the indicator element from its first position and allowing it to move into a second position in order to provide an indication of the presence of the contaminant; wherein the failure element is elongate in the sense that it is larger in the direction in which the indicator element moves on failure of the failure element than it is in any other dimension.

The device is based on simple chemistry and therefore cannot fail to work upon contact with the chemical to be detected. The device can be made very simple in construction allowing it to be produced very cheaply.

At present, when monitoring wells, it is necessary to take a sample from every well to determine whether or not contamination has occurred. With the present invention it would only be necessary to take samples from wells where the element has failed.

With the first aspect of the invention, as the failure element is held in tension, a failure, no matter how small, anywhere along the failure element, will cause the device to indicate the presence of a contaminant.

With the second aspect of the invention, as the failure element is elongate (for example, the length of the failure element in the direction in which the indicator element moves on failure is at least 3 times, preferably at least 10 times, more preferably at least 20 times, and most preferably at least 50 times its size in any other dimension), it can be extended across a zone in which chemical contaminant is to be detected, thereby providing a cost effective way of detection beyond a single location.

The indicator element may be held in the first position by a biasing force, the biasing force acting to move the indicator element to the second position upon failure of the failure element. Alternatively, the indicator element is held in the first position by a biasing force and wherein a further force, which is strong enough to override the biasing force is arranged to act on the indicator element to move it to the second position upon failure of the failure element.

In its simplest form the indicator element is a spring which is fixed to the failure element, the spring being under compression, such that the failure element is under tension. The failure element is preferably a tubular member. In order to provide a further degree of monitoring of the condition of the failure element, the tubular member is preferably sealed, the inside of the tubular member is maintained at a pressure other than atmospheric, and means are provided to monitor this pressure to determine the integrity of the tubular member. In order to operate a valve, a cable can pass through the tubular member and be fixed to one end of the spring such that, on failure of the failure element the cable is pulled through the tubular member to operate the valve. The spring is preferably attached to the failure element by a respective washer at each end of the spring, each washer being anchored to the failure element so as to be capable of movement in only one direction along the failure element. This allows the indicator element to be fastened in place with the necessary preload by pushing each washer along the failure element. The washer will then be held in place as the spring will tend to urge it in the direction in which it cannot move.

In order to assist with an assessment of the full extent of a chemical contaminant, the failure element is preferably made of a material which changes its appearance in the presence of the contaminant.

Preferably, the failure element is a tubular element and the indicator element is within the tubular element and is fixed at one end to the failure element, while its other end projects beyond the other end of the failure element and is biased away from the other end of the failure element.

The further force may be any type of force, such as a magnetic force. However, preferably, the failure element and indicator element are arranged to be supported vertically, wherein the further force is gravity.

In an alternative arrangement the indicator element comprises a core surrounded by a sleeve, the sleeve being biased away from the core, wherein the failure element holds the sleeve in a position in which it surrounds the core, whereby, when the failure element fails, the sleeve is released and moved away from the core providing a visual indication of the presence of the contaminant. Preferably, the outer surface of the sleeve is a different color from the outer surface of the core, thereby improving the visual indication of the presence of a contaminant.

In addition to the provision of visual indication, the device can also be arranged to operate some failsafe mechanism to prevent further contamination, such as by automatically closing a valve.

In its simplest form, the failure element is made of a single material which fails in the presence of a single contaminant. However, more complex devices are envisaged where the failure element comprises a number of different materials arranged in series and/or in parallel. With different materials arranged in series, the device will operate when any one of a number of contaminants to which a single material is responsive, is present. A parallel arrangement, on the other hand, will only fail when contaminants to which all of the materials are responsive are present. With a combination of series and parallel materials, a device can be tailored to detect a sophisticated selection of contaminants.

In order to detect the presence of a contaminant, several of the devices described above are arranged over the area, preferably in parallel. This allows a map of the location and extent of a contaminant to be created.

BRIEF DESCRIPTION OF THE DRAWINGS

Examples of devices constructed in accordance with the present invention will not be described with reference to the accompanying drawings, in which:

FIG. 1 is a schematic cross-section of a first example;
FIG. 2 is a cross-section of a second example;
FIG. 3 is a cross-section of a ground water monitoring well having a device according to the present invention;
FIG. 4 shows a device according to the present invention positioned under a tank in order to monitor leakage from the tank;
FIG. 4A is a detail of the part ringed as 4A in FIG. 4;
and
FIG. 5 is a schematic plan view showing the operation of FIG. 4 to determine the full extent of contaminant leakage.

DETAILED DESCRIPTION OF THE PREFERRED EMBODIMENT

The device shown in FIG. 1 comprises a tubular member 1 of high-density polystyrene. Attached to the tubular member 1 is a spring 2 which is held in compression by a pair of starlock washers 3 which anchor it to the tubular member 1. In the presence of a chemical contaminant, in this case any petroleum product, the tubular member 1 will fail and the spring 2 extends. The extension of the spring can be used to trigger a mechanical signal or alarm, or can close valves. A cable, such as a bowden cable, may extend through the tubular element and be fixed to one end of the starlock washers. On failure of the tubular member, the cable will be pulled through the tubular element allowing operation of a valve. The failure made may be shearing, stretching or bending of the tubular member, but is more likely to be slippage of a starlock washer when the surface of the tubular member has been degraded by the contaminant.

Figure 6:
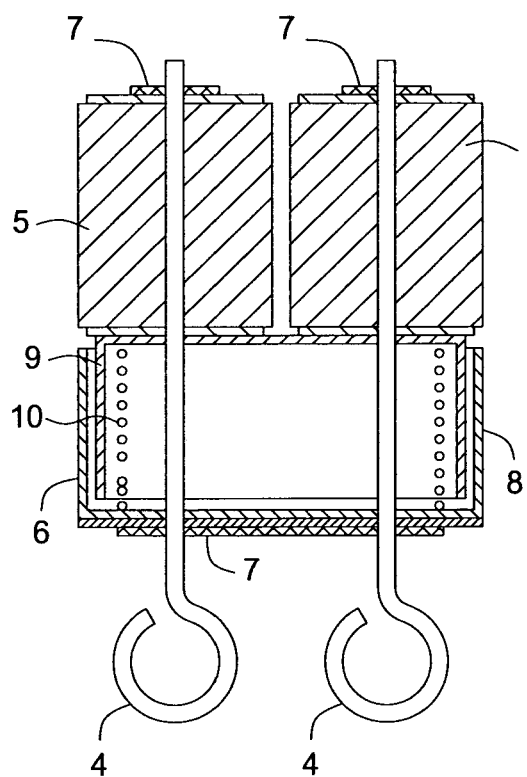
FIG. 6 is a cross-section of an example of the device.
Figure 7:
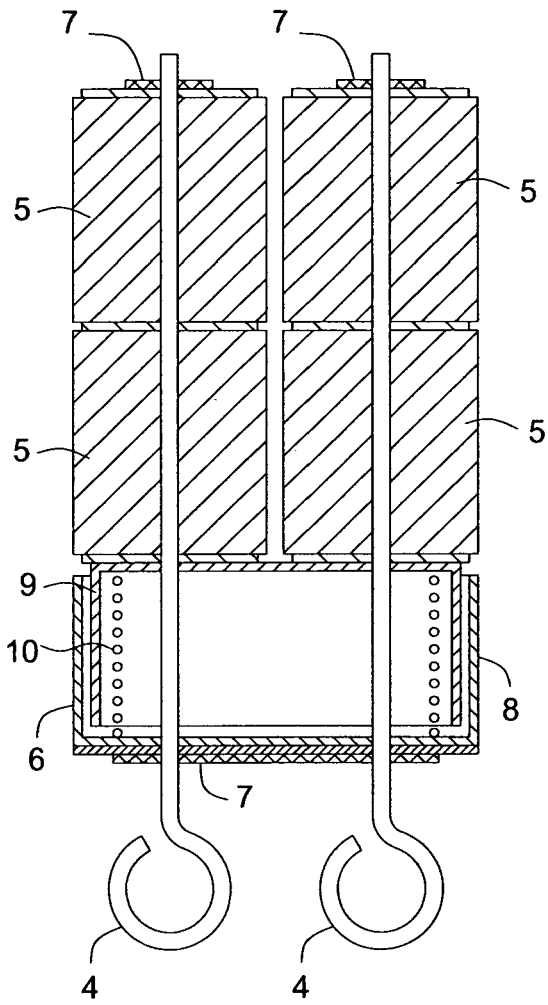
FIG. 7 is a cross-section of an example of the device.

A second example is shown in FIG. 2. In this case, the device is built around a central rod 4 on which are threaded three failure elements 5 of expanded polystyrene, and a resilient indicator element 6. The failure elements 5 and resilient indicator element 6 are held in place by a pair of starlock washers 7. The resilient indicator element 6 comprises a sleeve 8 surrounding a core 9. The sleeve 8 and core 9 are biased away from one another by compression spring 10. When any one of the failure elements 5 fails in the presence of a chemical contaminant, the compression of spring 10 forces the sleeve 8 and core 9 axially away from one another, so that the outer surface of the core 9 is uncovered providing a visual indication that failure has occurred. Other examples of the device are shown in FIG. 6 and FIG. 7.

A third example is shown in FIG. 3. This shows a device used in a ground water monitoring well which is buried below ground level 11. The well comprises a slotted or perforated well casing 12 closed at its top end by a well monitoring cap 13. In this case, the failure element 14 is a tubular member which is suspended from the cap 13 and fixed at its bottom end to a weight 15. The indicator element comprises an elongate rod 16 extending within the failure element 14 and attached at its lower end to the weight 15, and a spring 17 mounted in the cap 13 and acting to bias the rod 16 upwardly.

The lower part of the well is filled with ground water 18. If a chemical contaminant 19 is present floating on the ground water 18, this will react chemically with the failure member 14 causing it to fail. At this time, the full mass of the weight 15 is held by the rod 16 which will be pulled downwardly under gravity compressing spring 17 and providing a visual indication at the well cap of the presence of the contaminant.

When monitoring a well, the device could be several meters long, so that no matter at what level the hydrocarbon contaminant existed, the element would fail.

A fourth example is shown in FIGS. 4, 4A and 5. This example is designed to detect leakage from a tank 20. A plurality of elongate devices are buried in the ground 21 beneath the tank 20. FIG. 4 shows one such indicator, and the arrangement of all of the indicators is shown in plan in FIG. 5. The device comprises a perforated tube 22 containing elongate failure element 23 which projects from one end of the perforated tube 22 and is fastened at the other end of the tube 22. A spring 24 providing the indicator element is provided to bias a starlock washer 25 attached to the end of the failure element 23 away from a washer 26 at the end of the perforated tube 22 hence holding the failure element in tension.

When a chemical contaminant 27 leaks from the tank 20, it will enter the perforated tubes 22 immediately below the leak and will cause certain failure elements 23 to fail. Once a failure element 23 fails at any location, the spring 24 which is held in compression, will push the starlock washer 25 away from the end of the tube 22 thereby providing a visual indication of the presence of a contaminant. Once a contaminant is detected, all of the failure elements 23 can be pulled out and inspected. If they are made of a material which changes its appearance or is entirely obliterated in the presence of the contaminant, it is possible to build up a map showing the location and extent of the contaminant 27 as shown in FIG. 5.

While the foregoing is directed to embodiments of the present invention, other and further embodiments of the invention may be devised without departing from the basic scope thereof, and the scope thereof is determined by the claims that follow.

The invention claimed is:

1. A device for detecting the presence of a chemical leakage, the device comprising an indicator element which is held in a first position by means of a failure element which is held in tension, the failure element fails in the presence of the chemical leakage, thereby releasing the indicator element from its first position and allowing it to move into a second position in order to provide an indication of the presence of the leakage, wherein the failure element comprises a number of different materials for detecting different chemical leakages arranged in series and/or in parallel.

2. The device according to claim 1, wherein the indicator element is held in the first position by a biasing force, the biasing force acting to move the indicator element to the second position upon failure of the failure element.

3. The device according to claim 2, wherein the biasing force is provided by the resilience of the indicator element.

4. The device according to claim 3, wherein the resilient indicator element is a spring which is fixed to the failure element, the spring being under compression, such that the failure element is under tension.

5. The device according to claim 1, wherein the failure element is a tubular member.

6. The device according to claim 5, wherein the tubular member is sealed, the inside of the tubular member is maintained at a pressure other than atmospheric, and means are provided to monitor this pressure to determine the integrity of the tubular member.

7. The device according to claim 1, wherein the failure element is made of a material which changes its appearance in the presence of the leak.

8. The device according to claim 1, wherein the indicator element is held in the first position by a biasing force and wherein a further force, which is strong enough to override the biasing force is arranged to act on the indicator element to move it to the second position upon failure of the failure element.

9. The device according to claim 8, wherein the failure element and indicator element are arranged to be supported vertically, wherein the further force is gravity.

* * * * *